(12) United States Patent
Nevalainen et al.

(10) Patent No.: US 7,517,685 B2
(45) Date of Patent: Apr. 14, 2009

(54) GENE PROMOTERS

(75) Inventors: Helena Nevalainen, Pendle Hill (AU); Valentino Setoa Junior Te'O, Lane Cove (AU); Natalie Curach, Crows Nest (AU); Peter Leonard Bergquist, Auckland (NZ)

(73) Assignee: MacQuarie University, New South Wales (AU)

( * ) Notice: Subject to any disclaimer, the term of this patent is extended or adjusted under 35 U.S.C. 154(b) by 306 days.

(21) Appl. No.: 10/498,549

(22) PCT Filed: Dec. 13, 2002

(86) PCT No.: PCT/AU02/01692

§ 371 (c)(1),
(2), (4) Date: Feb. 22, 2005

(87) PCT Pub. No.: WO03/050233

PCT Pub. Date: Jun. 19, 2003

(65) Prior Publication Data

US 2005/0221474 A1 Oct. 6, 2005

(30) Foreign Application Priority Data

Dec. 13, 2001 (AU) .................................... PR9459

(51) Int. Cl.
*C12N 5/08* (2006.01)
(52) U.S. Cl. .................... 435/325; 435/320.1; 536/24.1
(58) Field of Classification Search ........................ None
See application file for complete search history.

(56) References Cited

U.S. PATENT DOCUMENTS 6,277,596 B1 * 8/2001 Watanabe et al. .......... 435/69.1

FOREIGN PATENT DOCUMENTS

| WO | WO 94/04673 | 3/1994 |
|---|---|---|
| WO | WO 00/56900 | 9/2000 |

OTHER PUBLICATIONS

Cannon et al. (1994) "Molecular cloning and expression of the *Candida albicans* beta-N-acetylglucosaminidase (HEX1) gene" *J. Bacteriol.* 176(9): 2640-2647.

Database Geneseq (Mar. 13, 2001) "*Trichoderma ressei* EST SEQ ID No. 7799" XP002331654 retrieved from EBI accession No. GSN: AAF15276 Database Accession No. AAF15276.

Jedd et al. (2000) "A new self-assembled peroxisomal vesicle required for efficient resealing of the plasma membrane" *Nature Cell Biology* 2: 226-231.

Kuhls et al. (1999) Molecular evidence that the asexual industrial fungus *Trichoderma reesei* is a clonal derivative of the ascomeycete *Hypocrea jecorina* 93: 775-7760.

Lim et al. (2001) "Proteins associated with the cell envelope of *Trichoderma reesei*: A proteomics approach" *Proteomics* 1(7): 899-910.

Mio et al. (1997) "Isolation of the *Candida albicans* homologs of *Saccharomyces cerevisiae* KRE6 and SKN1: Expression and physiological function" *J. Bacteriol.* 179: 2363-2372.

Pennington et al. (1999) "Characterization of VspB of *Borrelia turicatae*, a Major Outer Membrane Protein Expressed in Blood and Tissues of Mice" *Infection and Immunity* 67(9): 4637-4645.

Tenney et al. (2000) "Hex-1, a gene unique to filamentous fungi, encodes the major protein of the Woronin body and functions as a plug for septal pores" *Fungal Genetics and Biology* 31: 205-217.

* cited by examiner

*Primary Examiner*—James S Ketter
(74) *Attorney, Agent, or Firm*—Cooley Godward Kronish, LLP

(57) ABSTRACT

The invention is directed to a method for obtaining a promoter from an organism using a proteomics approach, isolated promoters from fungal species and uses of the isolated promoters.

11 Claims, 11 Drawing Sheets

Figure 2

```
   1 GCTAAGACTGCATGTGCATCACGAAAAGTGGGCGCTTGATAGTCCTCCTC   50
  51 CAGCCGGCATTGGCGAAGCAGGATAGACGATGGACAAGATGCAGCATCAG  100
 101 CTCGGACGGAGCCCTCCCTCCTGATGATAAGCCAAAACACTCTTCCGGT  150
 151 GGCGCCATGCAAGTACGGCGCATGTTGCTCGCAGAGCCAAGTGCAGTACC  200
 201 AGCAGAGCTGGATCATTACCCTACGACTTGGAAGCTGCTCGATTGGCACG  250
 251 GCTTGACATGGTCCCAACCCCTCAGGCTGGATGTATTTGTGCCTCGCACG  300
 301 CTCATCAGCGCCCTGTCCCAATGGCAATGAGTCTAGATTTGGCAGCAGCG  350
 351 ATGTATTATCGAACGGCCAGGCTCACTAGGCCAGGAACCAGTCCCGCCAC  400
 401 AGACTACCGACTGAGAGCGAGAAATAGAGAGAGGGGAGAAAGGCCACAGT  450
 451 TGTTATTACCCATGGAAATGGCTCGTAGCTGACCACAACAATGATGAGGA  500
 501 GACTGATGATTACGATGTACAGTACATACGTATTACCACTGCCACGAGTA  550
 551 CATACGCACGGGGTATTACAGCTGCTGTACCACCAGGTACGGTCGTGCTC  600
 601 GACGCTCATTACCGGTTTGATACTACTGGCACTAGCTGCAGAGGAGCCAT  650
 651 GAACATCAATCGCCCAGCCTGACTGGTCAATCAACGGCCGATTCAGGGGG  700
 701 GACGCAAGGGAAGCAGGGAAGCAAGGAGGCTGGGGAGCTCTTGGTCGCCC  750
 751 TTTGGGGTCCCATCCGCTTACCGCTGGGTTGCAGCATCATGTCCGAGGAG  800
 801 TCCACTGGCGACTGGAGACCCGAGTACGCCTGAGACGCAGCCTCGAGAGA  850
 851 CCAGTGGCCGAGACGCCTGCTGAGGCCGCTGAGCTTGCAGGGGAGTTGGA  900
 901 TGAGGTTGGCTGAGTGTGGGGACGATGGCGGAGACGAGAGGCCAGGATAC  950
 951 GACAGCACTAGGCCGGTTGTGACGAGAATAAACAACAACATGGCGAGTCC 1000
1001 CGGGGGCAGGTCGACATGGAGGGCCGATAGGCTTACCCTCCTTGGCGAGG 1050
1051 CAACACAGCGAGCACGCCTAGGACCGCCAGCCCGGCCCCCGACCTCAAAA 1100
```

Figure 2 Continued

```
1101 GCCCATCGAGCGTCGTCTGCTTCCGATCTGGTTTTCCTCTCCTCCAGTTA 1150
1151 TCACAGTCTCCCCGCCAGAAACAAAGGAACAAAAGAAAGAAAGACTCTC 1200
1201 AGAGGTATCCAATCCCTCTCTCTTTTCTCTCTCTCTTCGACTTTTGTTTC 1250
1251 AGGAACAAAAGCTTGAGGATCCTTCTTGTCTTCCTTTCGTGATCTTACGG 1300
1301 AAGGTTGTATGAGAAGATTCTCTCGCGCCAGCGCAAGCCGTCAACCTGGA 1350
1351 CTTTGAAGCCCGAGTTCCCGTGCCCTTTAGTATCTTCCCGTCCACTTACA 1400
1401 AGGACAACGAAGCAGCACGCCCTCAGACCCAAATCAGCGTTCACGAGGAG 1450
1451 GTTCAACTCACCCTCCCTCAACACAAGCCAGCCGGACGGGAGGGTCAACA 1500
1501 CTCTTCTTTCCCGCAACACGCCGACTCAGCTCCTCCTCGCGGCGAACACC 1550
1551 GCTTTGAAGAAGAGGTCCGTATCACGCGTGAGGAAGAACGTCACCGCCGT 1600
1601 CCCGGTTCCCGCCAGTCTGAACGCTTCGTGAAGGAAGAGTTCAAGTAAGT 1650
1651 TGATATTTCATTTTTCCCTGCTATTCATATTGTCTCCTGGCTGTGGCTCC 1700
1701 CGCCTCTCGTCTCCTCGCCAGACCGCTCTCACCGAGTGAGGGCAGCTGGG 1750
1751 GGAAAAGGGGGGAGAAAGGGATGGCCAAAGGGGTGAGGAGAGACGGGAGG 1800
1801 GAGAGCTGGGGAGGGGTGATGAGAACGCACGCAGCAATTACCGGCGTGGC 1850
1851 TGGCGAAAGCGGTGCTGAAATTACCCTTCGTATTGCCCTTCTTCCCACAC 1900
1901 AGCTCTTTTGCCGCGGCTTCTAGAACGCGTCAATTGATAGTGGGGAGGGC 1950
1951 AAGCCTGGGCACGGGGAGGGCGGCGGAGCTCACTATGGGGAGCTGACAGC 2000
2001 CGGGGTGGGAGTTCAGCTAGGATTCCCAGCCATGCCAATTTATCCCGGCT 2050
2051 CAGGGGGTCCGGGGGCCCACCAATGTTGGCCCAGAGACCAAGGAAGCTC 2100
2101 ACGCACAGGCACAAAAGGGAATCTCTCCAGCTAACCTCGAGTACTTTTAG 2150
2151 ATCCATCCCACCTCCTCCTCGCGACTACACTGAGACTCAAGTCCAAGTCG 2200
2201 ACACTTCTCGCCGCTACACCAACCCCATTGACGCTGCTGAGCGTGAGTAT 2250
```

Figure 2 Continued

```
2251 CGGGAACGTATCCGTCCTCACCACCCAGAGAGCTCCACCGGCCTCGAACT 2300

2301 AGTTGTTCGCCGTCCTCGTCACTCCGACAAGTCTCACCACCACCACCACC 2350

2351 ACAAGTCCTCCGACTTCACCGTTGTCGACGAGCACACTTCTGTTGCCCGT 2400

2401 CCCAAGTTCCGTGAGGAGATCAAGATCACCGAGGAAATCCGCGAGTCTAC 2450

2451 TCCGCAAGTCCCCGAACAATCCGCCAAGATG 2481
```

Figure 3

```
   1 GCTAAGACTGCATGTGCATCACGAAAAGTGGGCGCTTGATAGTCCTCCTC   50
  51 CAGCCGGCATTGGCGAAGCAGGATAGACGATGGACAAGATGCAGCATCAG  100
 101 CTCGGACGGAGCCCTCCCTCCTGATGATAAGCCAAAACACTCTTCCGGT  150
 151 GGCGCCATGCAAGTACGGCGCATGTTGCTCGCAGAGCCAAGTGCAGTACC  200
 201 AGCAGAGCTGGATCATTACCCTACGACTTGGAAGCTGCTCGATTGGCACG  250
 251 GCTTGACATGGTCCCAACCCCTCAGGCTGGATGTATTTGTGCCTCGCACG  300
 301 CTCATCAGCGCCCTGTCCCAATGGCAATGAGTCTAGATTTGGCAGCAGCG  350
 351 ATGTATTATCGAACGGCCAGGCTCACTAGGCCAGGAACCAGTCCCGCCAC  400
 401 AGACTACCGACTGAGAGCGAGAAATAGAGAGAGGGGAGAAAGGCCACAGT  450
 451 TGTTATTACCCATGGAAATGGCTCGTAGCTGACCACAACAATGATGAGGA  500
 501 GACTGATGATTACGATGTACAGTACATACGTATTACCACTGCCACGAGTA  550
 551 CATACGCACGGGGTATTACAGCTGCTGTACCACCAGGTACGGTCGTGCTC  600
 601 GACGCTCATTACCGGTTTGATACTACTGGCACTAGCTGCAGAGGAGCCAT  650
 651 GAACATCAATCGCCCAGCCTGACTGGTCAATCAACGGCCGATTCAGGGGG  700
 701 GACGCAAGGGAAGCAGGGAAGCAAGGAGGCTGGGGAGCTCTTGGTCGCCC  750
 751 TTTGGGGTCCCATCCGCTTACCGCTGGGTTGCAGCATCATGTCCGAGGAG  800
 801 TCCACTGGCGACTGGAGACCCGAGTACGCCTGAGACGCAGCCTCGAGAGA  850
 851 CCAGTGGCCGAGACGCCTGCTGAGGCCGCTGAGCTTGCAGGGGAGTTGGA  900
 901 TGAGGTTGGCTGAGTGTGGGGACGATGGCGGAGACGAGAGGCCAGGATAC  950
 951 GACAGCACTAGGCCGGTTGTGACGAGAATAAACAACAACATGGCGAGTCC 1000
1001 CGGGGGCAGGTCGACATGGAGGGCCGATAGGCTTACCCTCCTTGGCGAGG 1050
1051 CAACACAGCGAGCACGCCTAGGACCGCCAGCCCGGCCCCCGACCTCAAAA 1100
```

Figure 3 Continued

```
1101 GCCCATCGAGCGTCGTCTGCTTCCGATCTGGTTTTCCTCTCCTCCAGTTA 1150
1151 TCACAGTCTCCCCGCCAGAAACAAAGGAACAAAAGAAAGAAAAGACTCTC 1200
1201 AGAGGTATCCAATCCCTCTCTCTTTTCTCTCTCTCTTCGACTTTTGTTTC 1250
1251 AGGAACAAAAGCTTGAGGATCCTTCTTGTCTTCCTTTCGTGATCTTACGG 1300
1301 AAGGTTGTATGAGAAGATTCTCTCGCGCCAGCGCAAGCCGTCAACCTGGA 1350
1351 CTTTGAAGCCCGAGTTCCCGTGCCCTTTAGTATCTTCCCGTCCACTTACA 1400
1401 AGGACAACGAAGCAGCACGCCCTCAGACCCAAATCAGCGTTCACGAGGAG 1450
1451 GTTCAACTCACCCTCCCTCAACACAAGCCAGCCGGACGGGAGGGTCAACA 1500
1501 CTCTTCTTTCCCGCAACACGCCGACTCAGCTCCTCCTCGCGGCGAACACC 1550
1551 GCTTTGAAGAAGAGGTCCGTATCACGCGTGAGGAAGAACGTCACCGCCGT 1600
1601 CCCGGTTCCCGCCAGTCTGAACGCTTCGTGAAGGAAGAGTTCAAGTAAGT 1650
1651 TGATATTTCATTTTTCCCTGCTATTCATATTGTCTCCTGGCTGTGGCTCC 1700
1701 CGCCTCTCGTCTCCTCGCCAGACCGCTCTCACCGAGTGAGGGCAGCTGGG 1750
1751 GGAAAAGGGGGGAGAAAGGGATGGCCAAAGGGGTGAGGAGAGACGGGAGG 1800
1801 GAGAGCTGGGGAGGGGTGATGAGAACGCACGCAGCAATTACCGGCGTGGC 1850
1851 TGGCGAAAGCGGTGCTGAAATTACCCTTCGTATTGCCCTTCTTCCCACAC 1900
1901 AGCTCTTTTGCCGCGGCTTCTAGAACGCGTCAATTGATAGTGGGGAGGGC 1950
1951 AAGCCTGGGCACGGGGAGGGCGGCGGAGCTCACTATGGGGAGCTGACAGC 2000
2001 CGGGGTGGGAGTTCAGCTAGGATTCCCAGCCATGCCAATTTATCCCGGCT 2050
2051 CAGGGGGTCCGGGGGGCCCACCAATGTTGGCCCAGAGACCAAGGAAGCTC 2100
2101 ACGCACAGGCACAAAAGGGAATCTCTCCAGCTAACCTCGAGTACTTTTAG 2150
2151 ATCCATCCCACCTCCTCCTCGCGACTACACTGAGACTCAAGTCCAAGTCG 2200
2201 ACACTTCTCGCCGCTACACCAACCCCATTGACGCTGCTGAGCGTGAGTAT 2250
```

Figure 3 Continued

```
2251 CGGGAACGTATCCGTCCTCACCACCCAGAGAGCTCCACCGGCCTCGAACT 2300

2301 AGTTGTTCGCCGTCCTCGTCACTCCGACAAGTCTCACCACCACCACCACC 2350

2351 ACAAGTCCTCCGACTTCACCGTTGTCGACGAGCACACTTCTGTTGCCCGT 2400

2401 CCCAAGTTCCGTGAGGAGATCAAGATCACCGAGGAAATCCGCGAGTCTAC 2450
``` hex1fwd primer: 

```
2451 TCCGCAAGTCCCCGAACAATCCGCCAAGATGGGTTACTACGACGACGAGG 2500
                                 M  G  Y  Y  D  D  E  G

2501 GTaagctatactaacgttcttttgtctctctccctcccgctcttctcctc 2550

2551 cattccctccctgtctggccagacgcgtgcaagcatacgctaacgcgtgt 2600

2601 cgccggcaggcTCTTACCACTCCCTCAAGCACGGCGTCGCCAAGACGATC 2650
                 S  Y  H  S  L  K  H  G  V  A  K  T  I 2651 GACAAGCTGCTCCCTCATCACCACCACCATCACCACCACAGTGATCACCA 2700
      D  K  L  L  P  H  H  H  H  H  H  H  S  D  H  H 2701 CCACCACAGTGACCATCATGACCATAATAACACTACGATCACAGAGCACG 2750
      H  H  S  D  H  H  D  H  N  N  T  T  I  T  E  H  V 2751 TTGAAGTTGATGTTGTCCGCCACGATGCTAATCACTCGCGACGCGCAGCT 2800
        E  V  D  V  V  R  H  D  A  N  H  S  R  R  A  A 2801 CCCGCCACTGAGTCGCAGCCTCAGACTGTGTCCATCCCCTGCCACCACAT 2850
      P  A  T  E  S  Q  P  Q  T  V  S  I  P  C  H  H  I 2851 CCGCCTGGGTGACTTCCTGATGCTCCAGGGCCGACCATGCCAGGTCATCC 2900
      R  L  G  D  F  L  M  L  Q  G  R  P  C  Q  V  I 2901 GCATCTCGACCTCGTCCGCCACTGGCCAGTACCGCTACCTTGGTGTTGAC 2950
      R  I  S  T  S  S  A  T  G  Q  Y  R  Y  L  G  V  D 2951 CTCTTCACCAAGCAGCTGCACGAGGAGTCCTCCTTCATCTCCAACCCTGC 3000
        L  F  T  K  Q  L  H  E  E  S  S  F  I  S  N  P  A
```

Figure 3 Continued

```
3001 CCCCAGCGTTGTTGTCCAGACCATGCTCGGCCCCGTCTTCAAGCAGTACC 3050
      P  S  V  V  V  Q  T  M  L  G  P  V  F  K  Q  Y  R
hex1rev primer: ←―――――――――――――――――――――――――――――

3051 GCGTCCTCGACATGGCTGACGGCTACGTCACCGCCATGACCGAGACCGGC 3100
      V  L  D  M  A  D  G  Y  V  T  A  M  T  E  T  G

3101 GACGTCAAGCAGGGCCTCAAGGTCATTGACCAGTCCAACCTGTGGTCTCG 3150
      D  V  K  Q  G  L  K  V  I  D  Q  S  N  L  W  S  R

3151 TCTGCAGCAGGCTTTCGAGTCCGGCCGCGGCAGCGTCCGTGTCCTGGTCC 3200
      L  Q  Q  A  F  E  S  G  R  G  S  V  R  V  L  V  L

3201 TCAACGACGGCGGCCATGAGCTCGCTGTTGAGATGAAGGTCGTCCACGGC 3250
      N  D  G  G  H  E  L  A  V  E  M  K  V  V  H  G

3251 TCTCGCCTGTAAACAATCCTCTCGATGACATCTTTCGTGTCTAAGGGGA 3300
      S  R  L  *

3301 GGGTTTATTGTCCATCCATCCTATGGATATTCCAGGCTCGGATCAAGCCT 3350

3351 GAATAATGTGAAAAATACCCCATGGGCTTGGAGTGATACGTGGAACGGTT 3400

3401 TGTCATTTTTTTGGATCGGGCTGGGATGTATTTTGGTCATGAGGCAGAGT 3450

3451 GCCCAGTAGATAGGATCTACCTATGTGCAGCACTGTAATTTAAGATGGAT 3500

3501 TTTGCATAACTTTTTTCTTTGTGCCGCCCTTTGTGACATGCAGTGATGAT 3550

3551 GCATCGTGATGCATCGTGTTGTCATGGCTGTAAATCGTCCTCCCTGCGCA 3600

3601 GATCACAAGCAGTACACGTTGCCTCTTGACGCGTCGTCGTGTTAGACTAC 3650

3651 CTGCCTACCTACCCAATGTCTGCGTGTTGACATCAAGGTACCCGTCGCCA 3700

3701 GCGCACCGGTCATGGGATACATGGGGAAACCCCACAAGATTGCAGCAGCC 3750

3751 ACGATATTATACGATGCCCGACATGTGAGAGTCGATGGTCCTCTTTTTTC 3800

3801 CCTTGCTCCAAACCCCACTTGTCGCATCTGTAACGAGAGACTGACGTTGT 3850

3851 CTTGATATGAAGCAAGCATCGATTCAGAGACGAGGAAGCAACCAGCACTG 3900

3901 TGCTAACATGGCAACAAATACGAGACCAAGTGGTAGATATATTACAGAGC 3950
```

Figure 3 Continued

```
3951 ACATATAGGCATGTAAGCAATGAGGACCGGGCAGATAGGGGAATTGCTGG 4000
4001 AGATAACATGTAGGTAGCGCGACAAAAGAACCGGTGGGATCTGGATATAG 4050
4051 CCGACGAATGATGTGATACTAAACTTGAAGGAGGGGGGGGAGGGGAGAG 4100
4101 GGGGGATGAGGGCGGGGGAGATGAAAGGCCGGATAAGCAGAGGACCAGCA 4150
4151 GACGGTCCATGTTTTGTTGCGGTAGCAAACAACACAACCACGATGTTGAT 4200
4201 GTGCTCCAACGACTGGTTTTGATAAGGTGATTGTTTGTTTGCCTTGAGAT 4250
4251 ACGTCGGCTCTTACAGCTGTTGGCGTGTATATCTTGACATCATACATAAG 4300
4301 GACTCCCCCCCTTGTTGAATTGCTTTTCAGCGAAAAGACGTACGTAGTAC 4350
4351 TAGTAGGATATAACACGTAGCTAGGG  4376
```

GENE PROMOTERS

CROSS REFERENCE TO RELATED APPLICATIONS

This application is a National Stage Application of PCT/AU02/01692 filed Dec. 13, 2002, which claims priority to Australian Patent Application No. PR 9459, filed on Dec. 13, 2001, incorporated by reference herein in its entirety.

TECHNICAL FIELD

The present invention relates to methods for obtaining promoters for gene expression and new gene promoters, particularly promoters from fungal species.

DESCRIPTION OF THE TEXT FILE SUBMITTED ELECTRONICALLY

The contents of the text file submitted electronically herewith are incorporated herein by reference in their entirety: a computer readable format copy of the Sequence Listing (filename: ALLE_011_00US_SubSeqList_08_26_2008.txt, date recorded: Aug. 26, 2008, file size: 13 kilobytes).

BACKGROUND ART

Promoter regions are essential for driving and regulating gene expression. These stretches of DNA sequences are usually found upstream of the gene open reading frame. The key genetic elements in a promoter include enhancer sites, silencing sites, upstream activator sequences, transcription factor binding sites and RNA polymerase binding sites (e.g. Lewin, B., Genes V, Oxford University Press, 1994). These elements respond to the external environment of a given organism therefore regulating gene expression according to the growth conditions.

Strong promoters are required for efficient gene expression. Among the best promoters described for filamentous fungi so far include the *Trichoderma reesei* cellobiohydrolase 1 (cbh1) promoter (Ilmén, M. et al., 1996. Mol. Gen. Genet. 251, 451-460) and *Aspergillus niger* var. *awamori* glucoamylase A promoter (Ward, M. et al., 1990. Bio/Technology 8:435-440). However, both these promoters are inducible by an appropriate carbon source (eg. cellulose and starch respectively) and repressed by glucose (ie. regulated by catabolite repression). So far, natural constitutive or carbon catabolite repression insensitive promoters comparable in strength to the cbh1 and glaA have not been described.

Strategies described for promoter isolation include (i) the use of promoter probe vectors, where genomic DNA fragments are randomly cloned in front of a reporter gene which is expressed only when the cloned fragment contains promoter activity (e.g. Neve et al., 1979. Nature 277:324-325); (ii) isolation of genes and their promoters from gene libraries using hybridization based on gene specific probes (e.g. Vanhanen, S., et al., 1989. Curr. Genet. 15:181-186) or nucleic acid sequences deduced from amino acid sequences; (iii) differential hybridization of a gene bank with an induced and non-induced cDNA probe (e.g. Teeri et al., 1983. Bio/technology 1:696-699).

The present invention uses a new strategy termed proteome display for gene promoter isolation. This is different to the nucleic acid based strategies such as those listed above. Proteomic analysis typically involves separation of proteins in a sample by their isoelectric point and molecular mass (2-dimensional gel electrophoresis, 2-DE). The gels are then stained to visualize the protein spots and may be blotted onto a suitable membrane for further processing. The 2-DE technology enables separation of several hundreds of proteins in complex mixtures (O'Farrell, P. H., et al., 1975. J. Biol. Chem. 250:4007-4021) and detection of proteins that are highly expressed in an organism grown under given cultivation conditions (e.g. according to the carbon source). Protein spots in a proteomic display differ in their intensity reflecting the level they are expressed. Therefore, detection of a strongly expressed protein indicates a presence of a strong promoter driving the gene encoding that particular protein. Strongly expressed protein spots can be cut out and analyzed by mass spectrometry (Verrils, N. M., et al., 2000. Electrophoresis 21:3810-3822). The obtained amino acid sequence can be used to design oligonucleotide primers for Chromosome Walking PCR (Morris, D., et al., 1995. Appl. Environ. Microbiol. 61:2262-2269) in order to isolate the promoter from a particularly strongly expressed gene (protein). Protein identification involves comparison of the obtained peptides and/or amino acid sequences to databases available e.g. on the WWW. However, identification of a strongly expressed protein is not necessary for the isolation of the promoter driving its expression.

The hex1 gene encodes a hexagonal (HEX1) protein of the fungal Woronin body and is unique to filamentous fungi (Tenney, K., et al., 2000. Fungal. Genet. Biol. 31:205-217). The HEX1 protein was identified as a dominant protein in cell wall extracts prepared from *Trichoderma reesei* cultures grown on cellobiose-lactose-soybean extract medium or glucose as a carbon source, by 2-dimensional gel electrophoresis (Lim et al., 2001. Proteomics 1:899-910). Therefore, identification and isolation of the hex1 gene promoter based on a proteomic display provides a new strategy for promoter isolation and gene expression using a promoter not necessarily affected by carbon catabolite repression.

The present inventors have now devised methods for obtaining or detecting new promoters of genes.

DISCLOSURE OF INVENTION

In a first aspect, the present invention provides a method for detecting or obtaining a promoter for a gene from an organism, the method comprising:
(a) obtaining one or more proteins produced by the organism under desired conditions;
(b) obtaining amino acid sequence data on a protein;
(c) preparing one or more oligonucleotides based on the obtained amino acid sequence of the protein;
(d) treating genomic or chromosomal DNA from the organism with one or more oligonucleotides to obtain genomic or chromosomal DNA encoding the protein and its regulatory regions; and
(e) sequencing the obtained genomic or chromosomal DNA to detect or obtain the promoter of the gene encoding the protein.

Preferably, the organism is a microorganism such as bacterium, yeast, fungus or filamentous fungus. It will be appreciated, however, that the organism can be any cell type obtained from higher organisms such as animals including humans and plants Preferably step (a) is carried out by separating proteins produced by the organism under desired conditions to provide a proteomic display.

When obtaining promoters from microorganisms for example, it is desirable to culture the organism under conditions that may induce the expression of one or more proteins.

Such induction may be the supply of nutrients such as carbon source or environmental conditions such as heat, pH, starvation, and the like. After culture, proteins produced by the microorganism can be separated by any suitable means such as two dimensional polyacrylamide gel electrophoresis (2-D PAGE). Proteins of interest can be isolated and amino acid sequence data obtained from peptide fragments of the protein by known sequencing methods. Once the peptide information has been ascertained, oligonucleotide probes can be prepared that will hybridize to complementary DNA sequences of the gene encoding the protein. Genomic or chromosomal DNA from the organism is then treated by the oligonucleotides in order to obtain the DNA encoding the gene, and its promoter (regulatory areas), for example by using the Genomic Walking PCR. Once obtained, sequencing of the DNA can be carried out to provide information on the promoter and terminator region of the gene.

The standard methods for obtaining new genes is to use cDNA as the source of the genetic material. As cDNA is used by standard methods presently engaged in the art, gene promoters cannot not be obtained as cDNA does not include regulatory information or sequences. In contrast, as genomic or chromosomal DNA is used by the present invention, more information and useful sequences including promoters can be obtained.

In a second aspect, the present invention provides an isolated promoter obtained by the method according to the first aspect of the present invention.

The method according to the present invention has been used to obtain a new fungal promoter (as part of the gene designated hex1) that can promote transcription in fungal cells. Thus, the promoter of the invention can be used to express heterologous genes or other nucleic acid sequences in fungi.

Accordingly, in a third aspect the present invention provides an isolated hex1 promoter from filamentous fungi.

Preferably, the promoter is derived from fungal species selected from *Ophiostoma* sp, *Trichoderma* sp, *Aspergillus* sp., *Penicillium* sp., *Topylocladium* sp., *Fusarium* sp., *Chrysosporium* sp., *Magnaporthe* sp., *Neurospora* sp., *Claviceps* sp., *Mycosphaerella* sp., *Collectotrichum* sp. *Ustilago* sp., *Podospora* sp. and *Mucor* sp.

In a fourth aspect, the present invention provides an isolated fungal promoter having a nucleic acid sequence substantially as shown in FIG. 2 (SEQ ID NO:1), and/or sequences which hybridize to the sequence of FIG. 2 (SEQ ID NO:1), preferably under stringent conditions.

It will be appreciated that even though HEX1 proteins may exhibit a reasonable amount of homology, it is not guaranteed at all that the promoter regions share significant homology. Therefore, the alignment of the HEX1 proteins can be used as the starting point for obtaining similar or functionally equivalent promoters from other microbial sources.

In a preferred form, the isolated promoter comprises the DNA sequence of a fungal hex1 gene promoter wherein the DNA sequence is selected from the sequence set out in FIG. 2 (SEQ ID NO:1), or a part sequence of FIG. 2 (SEQ ID NO:1), which is sufficient to control expression of a gene of interest; or a nucleotide molecule having a sequence which will hybridize, preferably under stringent conditions, to the sequence of FIG. 2 (SEQ ID NO:1) and which is capable of controlling expression of a gene of interest.

In one form, the nucleotide molecule hybridizes to the sequence of FIG. 2 (SEQ ID NO:1) under high stringency hybridization conditions.

Preferably, the fungal promoter sequence that can promote expression of a heterologous gene in fungal cells. The full sequence of the hex1 gene from *Trichoderma reesei* is shown in FIG. 3 (SEQ ID NO:2; SEQ ID NO:3).

The invention also features an isolated nucleic acid having a sequence that hybridizes to FIG. 2 (SEQ ID NO:1) under stringent conditions or that is at least 70% (at least 80, 90, 95, or 99%) identical to the sequence of FIG. 2 (SEQ ID NO:1). The promoter sequence shown in FIG. 2 (SEQ ID NO:1) is capable of promoting transcription in a fungal cell when operably linked to an open reading frame. Promoter sequence of FIG. 2 (SEQ ID NO:1) is the portion of the promoter upstream of the hex1 gene open reading frame as shown in FIG. 3 (SEQ ID NO:2; SEQ ID NO:3).

In a fifth aspect, the present invention provides a vector or transformed cell which contains an isolated nucleic acid forming a promoter obtained by the method according to the present invention. Vectors include nucleic acid vectors, such as expression plasmids, or viral vectors.

The promoter sequences of the invention can be introduced into a variety of expression vectors for expressing exogenous proteins in cells including fungal cells. Such exogenous proteins include hydrolytic enzymes such as phytases, cellulases, xylanases, beta-glucanases, amylases, lipases and proteases and molecules of therapeutic/pharmaceutical importance such as antibodies, human growth factor, tissue plasminogen activator or any other polypeptide of commercial value. More specifically, the new promoter sequence and an open reading frame to which it is operably linked can be integrated into a genome to produce transgenic cells that express enzymes and therapeutic agents examples of which are listed above. Methods of delivering nucleic acids into a cell, whether for transient or stable expression, are well known in the art of molecular biology.

In sixth aspect, the present invention provides a recombinant DNA construct comprising a promoter according to the second, third or fourth aspects of the present invention operably linked to a gene of interest.

Preferably, the gene of interest is selected from an appropriate source for a particular characteristic. The appropriate source can be a microorganism of interest which has some metabolic or functional activity which can be utilized for a commercial or useful activity.

In seventh aspect, the present invention provides an expression system comprising a construct according to the sixth aspect of the present invention.

Expression systems are known to the art and include cells such as microorganisms containing the construct which are able to express a gene under the control of the promoter.

In an eighth aspect, the present invention provides use of a promoter according to the present invention in controlling the expression of a gene.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

BRIEF DESCRIPTION OF THE DRAWINGS

FIG. 2 shows nucleotide sequence of the hex1 promoter according to the present invention isolated from *Trichoderma reesei*. (SEQ ID NO:1)

FIG. 3 shows the 'PUBLISH' format (GCG, Wisconsin Package Version 8.1) of the *Trichoderma reesei* hex1 gene sequence. Highlighted in bold and underlined is the potential Kozak sequence important for ribosome binding site directing mRNA translation (Kozak, M. 1987. Nucleic Acids Res. 15: 8125-8148). The short intron sequence is shown in lower case. Location of the two consensus (code hop) primers (hex1fwd and hex1rev) are highlighted with arrows. (SEQ ID NO:2 is DNA sequence and SEQ ID NO:3 is the amino acid sequence).

MODE(S) FOR CARRYING OUT THE INVENTION

Definitions

Figure 1:
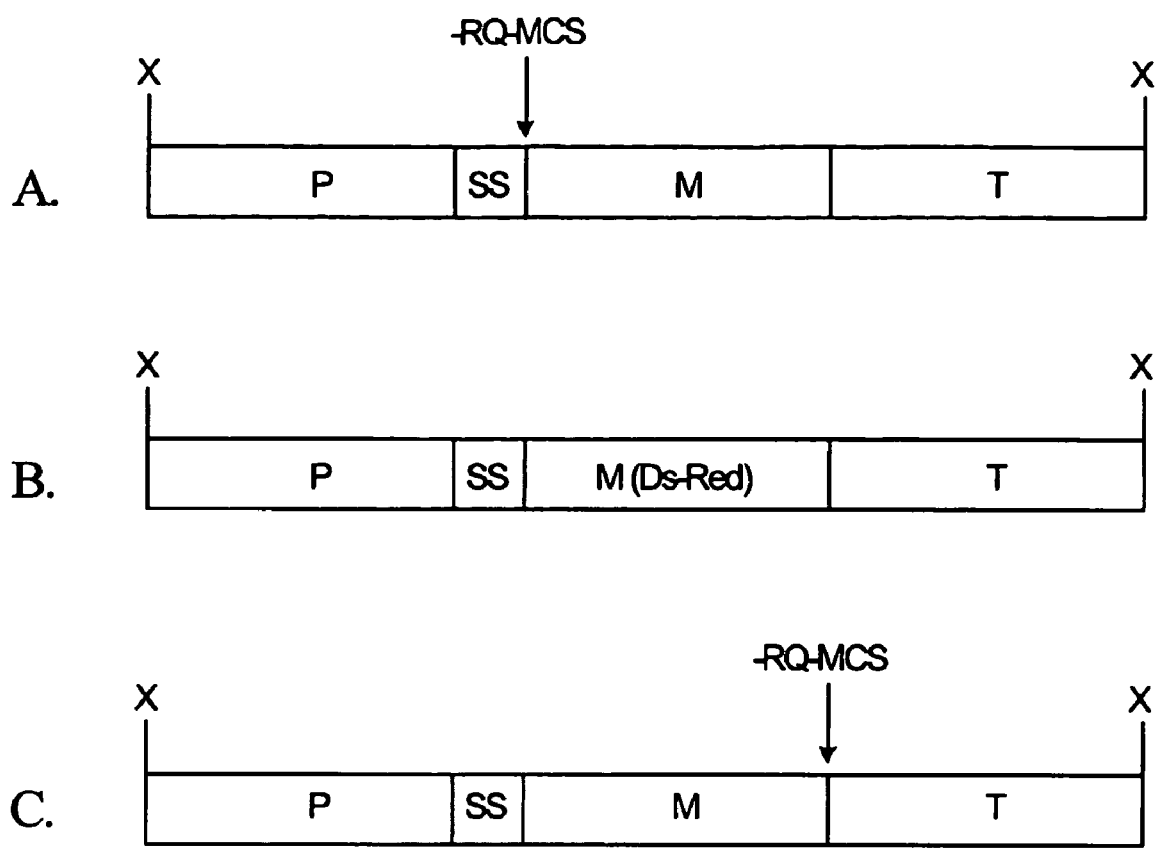
FIG. 1 shows the gene expression cassettes using the hex1 promoter. DNA fragments in a cassette are constructed using the plasmid pUC19 as the carrier for replication in E. coli. A. Basic expression vector with gene of interest linked or fused to the signal sequence. B. Expression vector to test hex1 gene promoter strength using the fluorescent dsRed1-E5 as a reporter gene. C. Expression vector with the gene of interest linked or fused to the transformation marker. Highlighted features include the hex1 gene promoter represented by P, secretion signal sequence, SS, proteolytic Kex2-like cleavage site, RQ, selectable marker gene, M (eg. fluorescent or antibiotic), and the hex1 gene terminator by T. Positions for restriction enzyme sites are shown by X.

With respect to equivalent sequences capable of hybridizing under high stringency conditions or having a high homology with nucleic acid molecules employed in the invention, "hybridizing under high stringency conditions" can be synonymous with "stringent hybridization conditions", a term which is well known in the art; see, for example, Sambrook, "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985; both incorporated herein by reference. With respect to nucleic acid molecules and polypeptides which can be used in the practice of the invention, the nucleic acid molecules and polypeptides advantageously have at least about 84 to 85% or greater homology or identity, such as at least about 85% or about 86% or about 87% or about 88% or about 89% homology or identity, for instance at least about 90% or homology or identity or greater, such as at least about 91%, or about 92%, or about 93%, or about 94% identity or homology, more advantageously at least about 95% to 99% homology or identity or greater, such as at least about 95% homology or identity or greater, at least about 96%, or about 97%, or about 98%, or about 99%, or even about 100% identity or homology, or from about 84 to about 100% or from about 90 to about 99 or about 100% or from about 95 to about 99 or about 100% identity or homology, with respect to sequences disclosed or described herein and fragments thereof herein disclosed or described (including subsequences discussed below).

Nucleotide sequence homology can be determined using the "Align" program of Myers and Miller, ("Optimal Alignments in Linear Space", CABIOS 4, 11-17, 1988, incorporated herein by reference). Alternatively or additionally, the term "homology" or "identity", for instance, with respect to a nucleotide or amino acid sequence, can indicate a quantitative measure of homology between two sequences. The percent sequence homology can be calculated as (N.sub.ref–N.sub.dif)*100/N.sub.ref, wherein N.sub.dif is the total number of non-identical residues in the two sequences when aligned and wherein N.sub.ref is the number of residues in one of the sequences. Hence, for instance the DNA sequence AGTCAGTC will have a sequence similarity of 75% with the sequence AATCAATC (N.sub.ref=8; N.sub.dif=2).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference). For instance, using a window size of 20 nucleotides, a word length of 4 nucleotides, and a gap penalty of 4, and computer-assisted analysis and interpretation of the sequence data including alignment can be conveniently performed using commercially available programs (Intelligenetics™ Suite, Intelligenetics Inc. California). When RNA sequences are said to be similar, or have a degree of sequence identity or homology with DNA sequences, thymidine (T) in the DNA sequence is considered equal to uracil (U) in the RNA sequence. RNA sequences within the scope of the invention can be derived from DNA sequences, by thymidine (T) in the DNA sequence being considered equal to uracil (U) in RNA sequences.

Additionally or alternatively, amino acid sequence similarity or identity or homology can be determined using the BlastP program (Altschul et al., Nucl. Acids Res. 25, 3389-3402, incorporated herein by reference). The following references (each incorporated herein by reference) also provide algorithms for comparing the relative identity or homology of amino acid residues of two proteins, and additionally or alternatively the teachings in these references can be used for determining percent homology or identity: Needleman S B and Wunsch C D, "A general method applicable to the search for similarities in the amino acid sequences of two proteins," J. Mol. Biol. 48:444-453 (1970); Smith T F and Waterman M S, "Comparison of Bio-sequences," Advances in Applied Mathematics 2:482-489 (1981); Smith T F, Waterman M S and Sadler J R, "Statistical characterization of nucleic acid sequence functional domains," Nucleic Acids Res., 11:2205-2220 (1983); Feng D F and Dolittle R F, "Progressive sequence alignment as a prerequisite to correct phylogenetic trees," J. of Mol. Evol., 25:351-360 (1987); Higgins D G and Sharp P M, "Fast and sensitive multiple sequence alignment on a microcomputer," CABIOS, 5:151-153 (1989); Thompson J D, Higgins D G and Gibson T J, "ClusterW: improving the sensitivity of progressive multiple sequence alignment through sequence weighing, positions-specific gap penalties and weight matrix choice, Nucleic Acid Res., 22:4673-480 (1994); and, Devereux J, Haeberlie P and Smithies O, "A comprehensive set of sequence analysis program for the VAX," Nucl. Acids Res., 12: 387-395 (1984).

The disclosed nucleic acid sequences or portions or fragments thereof, subsequences comprising at least about 12 nucleotides in length, for instance, at least about 15, about 18, about 21, about 24 or about 27 nucleotides in length, such as at least about 30, about 33, about 36, about 39 or about 42 nucleotides in length, for example, a nucleic acid molecule of at least about 12 nucleotides in length such as about 12 to about 30, about 12 to about 50 or about 12 to about 60, or about 12 to about 75 or about 12 to about 100 or more nucleotides in length may be useful in hybridization as probes or primers. The invention further comprehends microorganisms, vectors or plasmids containing and/or expressing such a nucleic acid molecule. As such, a nucleic acid molecule can encode an epitope or an epitopic region or a polypeptide which is functionally equivalent to polypeptides expressed by the sequences, well as uses of such nucleic acid molecules, for expression thereof either in vitro or in vivo, or for amplifying or detecting a defined gene or a homolog thereof, and the use of such vectors in new compositions.

The nucleic acids used for hybridization can, of course, be conveniently labeled by incorporating or attaching a radioactive or other detectable marker. Such markers are well known in the art. The labeling of said nucleic acid molecules can be effected by conventional methods. The presence or expression of the promoter or genes under control of the promoter can be monitored by using a primer pair that specifically hybridizes to either of the corresponding nucleic acid sequences and by carrying out a polymerase chain reaction (PCR) reaction according to standard procedures. Specific hybridization of the probes or primers preferably occurs at stringent hybridization conditions. A probe or primer can be any stretch of at least 8, preferably at least 10, more preferably at least 12, 13, 14, or 15, such as at least 20, at least 23 or 25, for instance at least 27 or 30 nucleotides in a defined nucleic acid molecule which are unique thereto. As to PCR or hybridization primers or probes and optimal lengths thereof, reference is also made to Kajimura et al., GATA 7(4):71-79 (1990), incorporated herein by reference.

Furthermore, expression of nucleic acid molecules under the control of a promoter according to the present invention are useful in generating antibodies which can be used to detect the presence or absence of the protein (or antigens thereof) in a sample or specimen; or, the expressed polypeptides can be used to detect the presence or absence of antibodies to proteins in a sample or specimen. Thus, nucleic acid molecules and expression products thereof have diagnostic utilities.

By "polypeptide" is meant any chain of amino acids, regardless of length or post-translational modification (glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By a "substantially pure polypeptide" is meant any polypeptide which has been separated from naturally accompanying components. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight. A substantially pure polypeptide may be obtained, for example, by extraction from a natural source (such as a cell); by expression of a recombinant nucleic acid encoding an the polypeptide; or by chemically synthesizing the protein. Purity can be measured by any appropriate method such as those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule under the control of a promoter according to the present invention encoding a given polypeptide.

By "positioned for expression" is meant that the DNA molecule is positioned adjacent to a DNA sequence defining a promoter which directs transcription and translation of the sequence (i.e., facilitates the production of a polypeptide, a recombinant protein or a RNA molecule).

By "reporter gene" is meant a gene whose expression may be assayed; such genes include, without limitation, beta-glucuronidase (GUS), luciferase, chloramphenicol transacetylase (CAT), and beta-galactosidase.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen, and microspores.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic fungi and the DNA (transgene) is inserted by artifice into the nuclear or plastidic genome.

By "conserved region" is meant any stretch of six or more contiguous amino acids exhibiting at least 30%, preferably 50%, and most preferably 70% amino acid sequence identity between two or more of the hex1 family members.

By "detectably-labelled" is meant any means for marking and identifying the presence of a molecule, an oligonucleotide probe or primer, a gene or fragment thereof, or a cDNA molecule. Methods for detectably-labeling a molecule are well known in the art and include, without limitation, radioactive labeling (with an isotope such as $^{32}P$ or $^{35}S$) and non-radioactive labeling (such as chemiluminescent labeling, or fluorescein labeling).

By "biolistic transformation" is meant any method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (chloroplasts and mitochondria), bacteria, yeast, fungi, algae, pollen, animal tissue, plant tissue (leaf, seedling, embryo, epidermis, flower, meristem, and root), pollen, and cultured cells.

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody. A purified antibody may be obtained, for example, by affinity chromatography using recombinantly-produced proteins or conserved motif peptides and standard techniques.

By "specifically binds" is meant an antibody which recognizes and binds an a protein but which does not substantially recognize and bind other molecules in a sample, a biological sample, which naturally includes rps protein.

Materials and Methods

Isolation of the hex1 Promoter from *Trichoderma reesei*

The HEX1 protein was identified as a strongly expressed protein in cell wall extracts prepared from *Trichoderma reesei* cultures grown on cellobiose-lactose-soybean extract medium or glucose as a carbon source, by 2-dimensional gel electrophoresis (Lim et al., 2001. Proteomics 1:899-910). The fungal hex1 gene promoter was isolated from *T. reesei* genomic DNA using the Chromosome Walking PCR procedure (Morris et al., 1985. Appl. Environ. Microbiol. 61:2262-2269). Initially, two consensus (code hop) primers (hex1fwd.pr: 5'-ACA TCT TCC AAA ATG GUN TAY TAY GA -3'(SEQ ID NO: 4) and hex1rev.pr: 5'-ACG GGG CCG CAC ATN GTY TUN AC-3'(SEQ ID NO: 5)) were designed based on nucleotide translation of conserved amino acid sequences from an alignment of HEX1 peptide sequences (Lim et al., 2001. Proteomics 1:899-910; Jedd and Chua, 2000. Nature Cell Biology 2:226-231). PCR amplification was carried out using the following conditions: [1×] 94° C., 10 mins [5×] 94° C., 30 s; 40° C., 30 s; 72° C., 30 s [35×] 94° C., 30 s; 50° C., 30 s; 72° C., 30 s. One unit of heat activated Amplitaq Gold Polymerase (Perkin and Elmer, USA) was used in a 50 µl PCR reaction containing the following ingredients: 100 ng of each of the two primers, 3 mM $MgCl_2$, 12.5 mM dNTP's and about 10 ng of target fungal genomic DNA.

A PCR product of about 600 bp was obtained from using the two consensus primers described above, and sequenced using the ABI 377 sequencing facility at Macquarie University, Australia. New 5'- and 3'-chromosomal walking primers were designed on the 600 bp hex1 sequence and were used in PCR reactions to obtain overlapping hex1 gene fragments. Further primers were designed and used to obtain upstream and downstream DNA fragments until all of the hex1 gene coding region, as well as sufficient promoter and terminator region DNA fragments were amplified and sequenced. A *T. reesei* genomic DNA-linker library was prepared first as described in Morris et al., 1985. Appl. Environ. Microbiol. 61:2262-2269, before Genomic Walking PCR reactions were carried out using the combination of either the forward or reverse chromosomal walking primer with the appropriate linker primer. PCR conditions used were as follows: [1×] 94° C., 10 min [40×] 94° C., 30 s; 60-65° C., 30 s; 72° C., 4-5 min. PCR ingredients described above were also used in the chromosomal walking PCR reactions.

The HEX1 protein sequence is highly conserved in filamentous fungi which enables isolation of the hex1 gene promoter from other filamentous fungi (such as those listed herein) using a procedure analogous to that described for *Trichoderma*.

It will be appreciated from this working example that promoters for other genes can be detected using the method according to the present invention. Using the primers devised for obtaining the hex1 gene of *T. reesei*, the present inventors have determined that the hex1 gene from *Ophiostoma floccosum* has a consensus DNA region of about 747 bp. Having obtained the genomic DNA for *O. floccosum*, it is possible to isolate the Hex1 promoter from this organism.

Construction of Plasmids for Gene Expression and Product Secretion

Plasmids can be constructed for expression of any chosen gene or nucleic acid under the hex1 promoter. For the purpose of cloning a particular gene of interest under the isolated hex1 promoter, a multicloning site will be added. The vector will also comprise a suitable selection marker functional in the expression host. Sufficient flanking DNA fragments for hex1 are included to promote integration at the homologous genomic locus if applicable. Unique restriction sites can be incorporated so that removal of the pUC19 vector portion will be carried out first before the linear expression DNA fragments are isolated and transformed into the fungal host. A suitable signal for protein secretion will be included. The secretion signal may be homologous or heterologous to the gene product of interest. Such signals are available, for example, from the genes encoding *Ophiostoma* protease and lipase and the *T. reesei* cbh1 or from any highly secreted or produced fungal protein). Expression cassettes can have sequences for the correct cleavage of the signal peptide by the signal peptidase resulting in secretion of the protein of interest outside of the cultivation medium. Following transformation, resulting transformants will be screened to isolate the transformants producing highest yields of the gene product of interest and analyzed in detail. It will be appreciated that such screening is routine testing known to the art.

Expression of the Heterologous DsRed1-E5 Protein Under the hex1 Promoter

The cloned hex1 promoter(s) is linked to the gene encoding DsRed1-E5 (Clontech). This provides an example of a heterologous protein expressed under the hex1 promoter and can be applied, for example, to further test the functionality of the hex1 promoter in different growth media (eg. glucose, lactose, cellulose). DsRed1-E5 is a mutant of the red fluorescent protein DsRed1 (Terskikh et al., 2000. Science 290:1585-1588) which increases its fluorescence intensity and causes the protein to change its fluorescence from green to red, as it matures. Level or intensity of fluorescence exhibited by the transformants should give a good indication of the amount of the secreted DsRed1-E5 protein. Culture supernatants will be further analyzed on SDS-PAGE gels. The use of DsRed1-E5 as a reporter will also allow comparison between different promoters. Finally, the gene of interest intended to be expressed in the host, can be expressed as a fusion protein to the DsRed1-E5 as indicated in FIG. 1.

FIG. 1 shows the gene expression cassettes using the hex1 promoter. DNA fragments in a cassette are constructed using the plasmid pUC19 as the carrier for replication in *E. coli*. A Basic expression vector with gene of interest linked or fused to the signal sequence. B. Expression vector to test hex1 gene promoter strength using the fluorescent dsRed1-E5 as a reporter gene. C. Expression vector with the gene of interest linked or fused to the transformation marker. Highlighted features include the hex1 gene promoter represented by P, secretion signal sequence, SS, proteolytic Kex2-like cleavage site, RQ, selectable marker gene, M (eg. fluorescent or antibiotic), and the hex1 gene terminator by T. Positions for restriction enzyme sites are shown by X.

Characterisation of the hex1 Gene and its Promoter

The hex1 gene sequence with the 5' and 3' flanking regions, isolated from *Trichoderma reesei* using Chromosome Walking PCR, is shown in FIG. 3. Amino acid translation of the 4376 bp nucleotide sequence in all six possible open reading frames revealed an open reading frame of 784 bp corresponding to the HEX1 starting methionine (ATG) at position 2479 and ending at the stop codon (TAA) position 3262 (FIG. 3). A short intron sequence exists between positions 2503 and 2612 corresponding well to the predicted consensus splicing sequences (e.g. Ballance, D.J., 1986. Yeast 2:229-236). Detailed analysis of the promoter region (FIG. 3) showed no clear 'TATA'-like box upstream of the ATG. Also, no prokaryotic-like Shine Dalgamo sequence (5'-AGGAGGACAGC-UAUG-3') (SEQ ID NO 10) can be detected. However, a potential ribosomal binding site located immediately upstream and including the starting ATG fits the consensus for eukaryotic initiation site, also called Kozak sequence (5'-A/GCCACCAUGG-3') (SEQ ID NO 11).

FIG. 3 shows the 'PUBLISH' (GCG, Wisconsin Package Version 8.1) format of the *Trichoderma reesei* hex1 gene sequence. Highlighted in bold and underlined is the potential Kozak sequence important for ribosome binding site directing mRNA translation (Kozak, M. 1987. Nucleic Acids Res. 15: 8125-8148). The short intron sequence is shown in lower case. Location of the two consensus (code hop) primers (hex1fwd and hex1rev) are highlighted with arrows.

Analysis of the hex1 gene terminator region (position 3263 to 4376) showed several perfect inverted repeat (palindrome) sequences which promotes termination of transcription by forming loops, stopping the RNA Polymerase II from transcribing further (e.g. Lewin, B., Genes V, Oxford University Press, 1994). One example is the sequence -CCCCATG- (position 3368 to 3374) with it's a perfect palindrome sequence of -GGGGTAC- found at position 3726 to 3720 (FIG. 3).

Alignment of HEX1 peptide sequences from a number of organisms have been carried out which demonstrated that the are a number of well conserved amino acids amongst. This homology at the protein level allows isolation of the hex1 promoter from a number of filamentous fungi by Chromosome Walking PCR.

Detailed peptide analysis showed the HEX1 from *T. reesei* to have 225 amino acids in length with an expected molecular weight of 25207 and an isoelectric point of 7.09. A high degree of amino acid homology was found between HEX1 from *T. reesei* and others submitted in the genbank database.

FIG. 2 shows the nucleotide sequence of the promoter of HEX1 protein from *Trichoderma reesei*.

Isolation of hex1 Gene Consensus DNA Fragment from *Ophiostoma floccosum*

A DNA fragment of 747 bp long was amplified from *Ophiostoma floccosum* (strain J3301) using the two consensus (code hop) primers (hex1fwd.pr:5'-ACA TCT TCC AAA ATG GGN TAY TAY GA-3'(SEQ ID NO 4) and hex1rev.pr: 5'-ACG GGG CCG CAC ATN GTY TGN AC-3'(SEQ ID NO 5)) in a PCR amplification reaction using Hot Star Taq DNA Polymerase (QIAGEN, Germany). The PCR conditions used were [1×] 95°C., 15 mins [5×] 95° C., 30 s; 40° C., 30 s; 72° C., 30 s [35×]95° C., 30 s; 50° C., 30 s; 72 ° C., 30 s. A 50 µL PCR reaction contained 0.25 units of Polymerase and 100 ng of each of the two primers, 1.5 mM $MgCl_2$, 12.5 mM dNTPs and about 10 ng of target *O. floccosum* genomic DNA. The 747 bp DNA fragment was gel-purified (QIAGEN, Germany) and sequenced using the ABI 377 sequencing facility at Macquarie University, Australia.

Total RNA Isolation and mRNA Northern Analysis

The Trizol method (Invitrogen, USA) was used to extract total RNA from mycelia removed from cultures grown in minimal medium (Pentillä et al., 1987. Gene. 61: 155-164) supplemented with 2% glucose as well as 1% cellobiose, 1% lactose and 3% soybean hydrolysate as carbon sources. Total RNA were denatured with Glyoxal and Dimethyl Sulfoxide and electrophoresed as described in Sambrook et al. 1989. Molecular Cloning: A Laboratory Manual, $2^{nd}$ edn. Cold Spring Harbor Laboratories Press, NY. After electrophoresis, RNA was transferred onto Hybond positive charged membrane (Roche, Germany) using the Biorad vacuum blotter (BioRad, USA) following the manufacturers instructions.

DNA hybridization probes were generated by PCR using the PCR DIG labeling mix (Roche, Germany). The primers for amplification of a 240 bp DsRed1-E5 DNA probe were dsredprobe.fwdpr:5'-CCA CCG AGC GCC TGT ACC -3' (SEQ ID NO 6) and dsredprobe.revpr:5'-CTA CAG GAA CAG GTG GTG -3 (SEQ ID NO 7). The 615 bp hex1 DNA probe was PCR generated with primers hexprobe2.fwdpr:5'-CCT CAA GCA CGG CGT CGC C-3' (SEQ ID NO 8) and hexprobe2.revpr:5'- CCT TCA TCT CAA CAG CGA GC-3' (SEQ ID NO 9). The PCR conditions were as follows: [1×] 94° C., 10 mins [35×] 94° C., 30 s; 50° C. 30 s; 72° C. 30 s [1×] 72° C., 5 mins. One unit of heat activated Amplitaq Gold Polymerase (Perkin and Elmer, USA) was used in a 50 µL PCR reaction containing the following ingredients: ~10 ng of target DNA, 100 ng of each of the two primers, 3 mM $MgCl_2$, 1×DIG labeled dNTP's. The DIG Luminescent Detection Kit for Nucleic Acids (Roche, Germany) was used to detect gene specific mRNAs following the protocol supplied by the manufacturer. Overnight hybridization with the two gene DNA probes were carried out at temperatures of 55° C. for the detection of DsRed1-E5 message and at 60° C. for hex1.

SUMMARY

In general, there is a shortage of efficient fungal gene promoters that can be used for the expression of homologous and heterologous gene products of interest. Gene promoters used for recombinant expression can be roughly divided in two categories, inducible and constitutive. Among the strongest inducible promoters, regulated by carbon catabolite repression, are the glucoamylase A promoter (glaA) of *A. niger* var. *awamori* (Ward, M. et al, 1990. Bio/Technology 8:435-440) and the *T. reesei* cellobiohydrolase 1 (cbh1) promoter (Ilmén, M. et al., 1996. Mol. Gen. Genet. 251, 451-460). A constitutive promoter used across fungal species is the *A. nidulans* glyceraldehyde-3-phosphate dehydrogenase gpdA (Punt et al. 1991. J Biotechnol 17:19-34). So far, natural constitutive or carbon catabolite repression insensitive promoters comparable in strength to the cbh1 and glaA have not been described.

Figure 4:
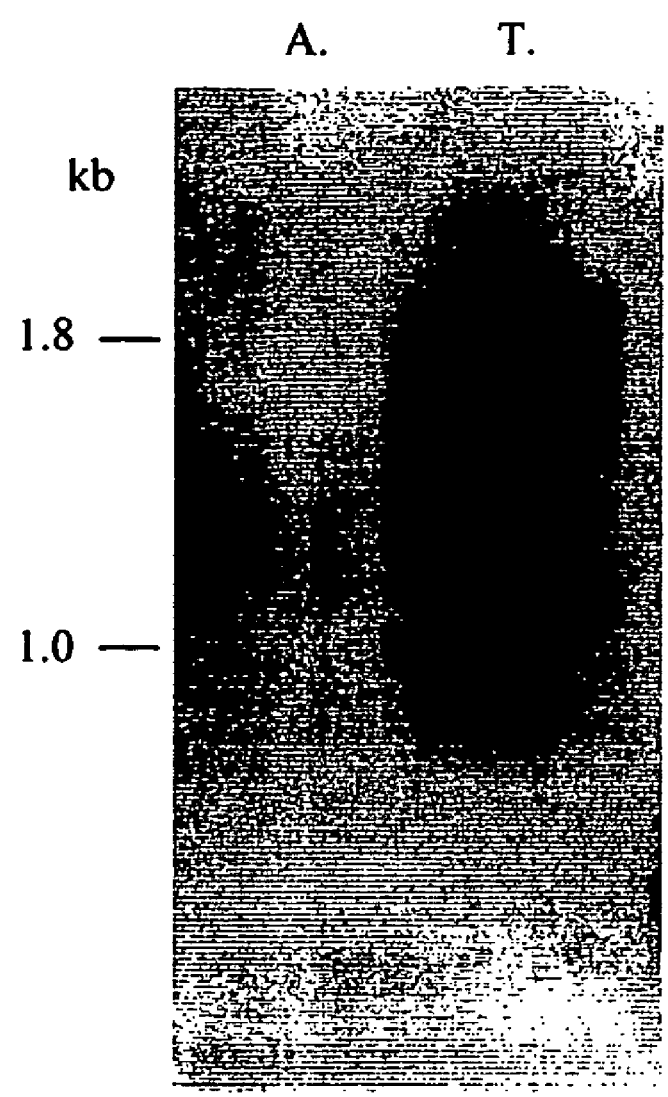
FIG. 4 shows a Northern blot showing expression of a heterologous gene under the hex1 promoter. Northern blot probed with DsRed1-E5 DNA. A, non-transformant; T, transformant containing the DsRed1-E5 gene under the *T. reesei* hex1 promoter. Cultures were grown for 54 hours in a medium containing cellobiose, lactose and soy hydrolysate (CLS).
Figure 5:
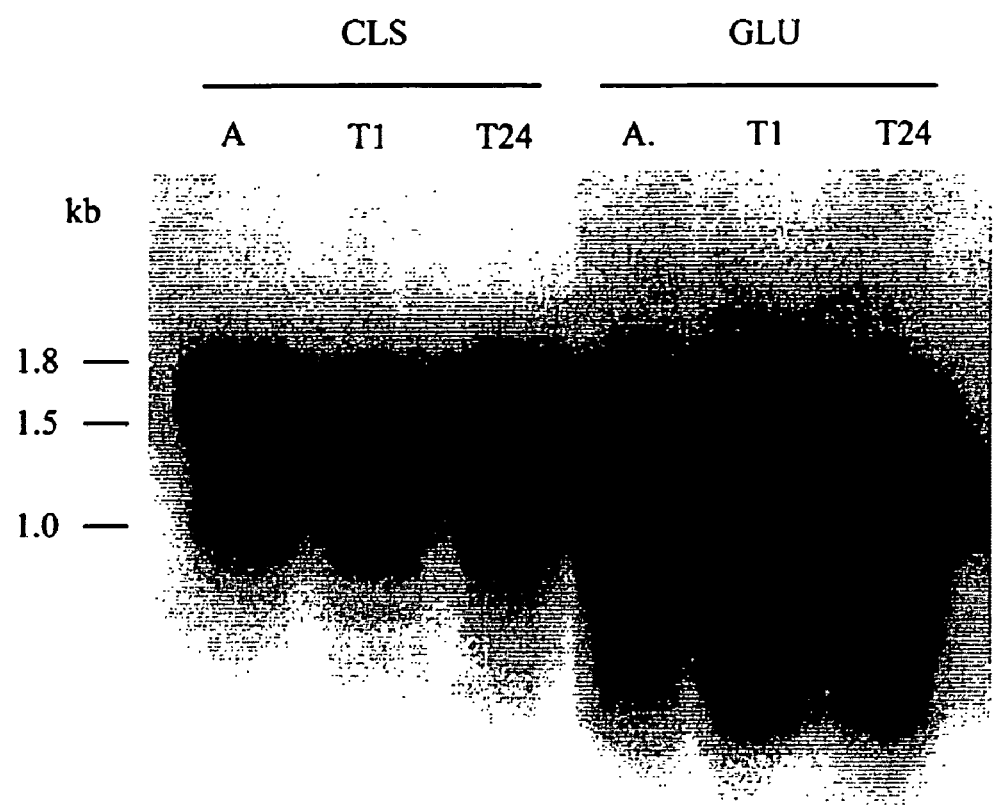
FIG. 5 shows a Northern blot of expression of hex1 in different cultivation media. Northern blot probed with hex1. A, non-transformant. T1 and T24, transformants containing the DsRed1-E5 gene under the hex1 promoter. Cultures were grown for 54 hours in CLS or glucose (GLU) medium.

The present inventors have shown that the 2-D proteomic display can be used to identify promoters such as the *T. reesei* hex1 promoter that are highly functional under specified circumstances such as on glucose medium that mediates catabolite repression. The hex1 gene promoter is also functional under conditions that promote induction of cbh1 (see FIG. 4 and FIG. 5 showing hex1 expression on glucose and CLS). Further to demonstrate the use of hex1 promoter in heterologous gene expression, the present inventors have shown expression of the DsRed-51 gene from sea anemone under the hex1 promoter (see FIG. 5). In summary, hex1 promoter provides a versatile option for gene expression and contributes to the suitability of a fungal expression system. The 2-D strategy for promoter isolation according to this invention can be applied to any fungus (or any other organism) and any cultivation condition that is beneficial for the production of a particular gene product of interest.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An isolated hex 1 promoter of *Trichoderma reesei*, having a nucleotide sequence substantially as shown in SEQ ID NO: 1, a nucleotide sequence which hybridizes to the nucleotide sequence as shown in SEQ ID NO: 1 under stringent conditions, or having a functional part of the sequence shown in SEQ ID NO: 1 which is capable of controlling expression of a gene when in a fungal species.

2. The hex1 promoter according to claim 1 having the nucleotide sequence substantially as shown in SEQ ID NO: 1.

3. The hex1 promoter according to claim 1 having a nucleotide sequence which hybridizes to the sequence of SEQ ID NO:1 under high stringency hybridization conditions.

4. A vector or transformed cell which contains the isolated hex1 promoter according to claim 1.

5. The vector according to claim 4 selected from the group consisting of nucleic acid vector, plasmid, and viral vector.

6. A recombinant DNA construct comprising the isolated hex1 promoter according to claim 1 operably linked to a gene.

7. The DNA construct according to claim 6 wherein the gene encodes a protein.

8. The DNA construct according to claim 7 wherein the protein is selected from the group consisting of an hydrolytic enzyme, and molecule suitable for therapeutic or pharmaceutical use.

9. The DNA construct according to claim 8 wherein the hydrolytic enzyme is selected from the group consisting of phytases, cellulases, xylanases, beta-glucanases, amylases, lipases, and proteases.

10. The DNA construct according to claim 8 wherein the molecule suitable for therapeutic or pharmaceutical use is selected from the group consisting of proteins, antibodies, growth factors, growth inhibitors, and tissue activators.

11. An expression system containing the DNA construct according to claim 7.

* * * * *

SEQUENCE LISTING

<160> NUMBER OF SEQ ID NOS: 3

<210> SEQ ID NO 1
<211> LENGTH: 2481
<212> TYPE: DNA
<213> ORGANISM: Trichoderma reesei

<400> SEQUENCE: 1

```
gctaagactg catgtgcatc acgaaaagtg ggcgcttgat agtcctcctc cagccggcat     60
tggcgaagca ggatagacga tggacaagat gcagcatcag ctcggacgga gccctccctc    120
cctgatgata agccaaaaca ctcttccggt ggcgccatgc aagtacggcg catgttgctc    180
gcagagccaa gtgcagtacc agcagagctg gatcattacc ctacgacttg gaagctgctc    240
gattggcacg gcttgacatg gtcccaaccc ctcaggctgg atgtatttgt gcctcgcacg    300
ctcatcagcg ccctgtccca atggcaatga gtctagattt ggcagcagcg atgtattatc    360
gaacggccag gctcactagg ccaggaacca gtcccgccac agactaccga ctgagagcga    420
gaaatagaga gaggggagaa aggccacagt tgttattacc catggaaatg gctcgtagct    480
gaccacaaca atgatgagga gactgatgat tacgatgtac agtacatacg tattaccact    540
gccacgagta catacgcacg gggtattaca gctgctgtac caccaggtac ggtcgtgctc    600
gacgctcatt accggtttga tactactggc actagctgca gaggagccat gaacatcaat    660
cgcccagcct gactggtcaa tcaacggccg attcaggggg gacgcaaggg aagcagggaa    720
gcaaggaggc tggggagctc ttggtcgccc tttggggtcc catccgctta ccgctgggtt    780
gcagcatcat gtccgaggag tccactggcg actggagacc cgagtacgcc tgagacgcag    840
cctcgagaga ccagtggccg agacgcctgc tgaggccgct gagcttgcag gggagttgga    900
```

```
tgaggttggc tgagtgtggg gacgatggcg gagacgagag gccaggatac gacagcacta      960
ggccggttgt gacgagaata acaacaaca tggcgagtcc cggggcagg tcgacatgga      1020 gggccgatag gcttaccctc cttggcgagg caacacagcg agcacgccta ggaccgccag     1080
cccggccccc gacctcaaaa gcccatcgag cgtcgtctgc ttccgatctg gttttcctct    1140
cctccagtta tcacagtctc cccgccagaa acaaaggaac aaaagaaaga aagactctc     1200 agaggtatcc aatccctctc tcttttctct ctctcttcga cttttgtttc aggaacaaaa    1260
gcttgaggat ccttcttgtc ttcctttcgt gatcttacgg aaggttgtat gagaagattc    1320
tctcgcgcca gcgcaagccg tcaacctgga ctttgaagcc cgagttcccg tgcccttag     1380 tatcttcccg tccacttaca aggacaacga agcagcacgc cctcagaccc aaatcagcgt    1440
tcacgaggag gttcaactca ccctccctca acacaagcca gccggacggg agggtcaaca    1500
ctcttctttc ccgcaacacg ccgactcagc tcctcctcgc ggcgaacacc gctttgaaga    1560
agaggtccgt atcacgcgtg aggaagaacg tcaccgccgt cccggttccc gccagtctga    1620
acgcttcgtg aaggaagagt tcaagtaagt tgatatttca tttttccctg ctattcatat    1680
tgtctcctgg ctgtggctcc cgcctctcgt ctcctcgcca gaccgctctc accgagtgag    1740
ggcagctggg ggaaaagggg ggagaaaggg atggccaaag gggtgaggag agacgggagg    1800
gagagctggg gaggggtgat gagaacgcac gcagcaatta ccggcgtggc tggcgaaagc    1860
ggtgctgaaa ttaccctttcg tattgcccctt cttcccacac agctcttttg ccgcggcttc   1920
tagaacgcgt caattgatag tgggggggc aagcctgggc acggggaggg cggcggagct    1980
cactatgggg agctgacagc cggggtggga gttcagctag gattcccagc catgccaatt    2040 tatccccggct caggggtcc gggggcccca ccaatgttgg cccagagacc aaggaagctc    2100
acgcacaggc acaaaaggga atctctccag ctaacctcga gtactttag atccatccca     2160 cctcctcctc gcgactacac tgagactcaa gtccaagtcg acacttctcg ccgctacacc    2220
aaccccattg acgctgctga gcgtgagtat cgggaacgta tccgtcctca ccacccagag    2280
agctccaccg gcctcgaact agttgttcgc cgtcctcgtc actccgacaa gtctcaccac    2340
caccaccacc acaagtcctc cgacttcacc gttgtcgacg agcacacttc tgttgcccgt    2400
cccaagttcc gtgaggagat caagatcacc gaggaaatcc gcgagtctac tccgcaagtc    2460
cccgaacaat ccgccaagat g                                              2481
```

<210> SEQ ID NO 2
<211> LENGTH: 4376
<212> TYPE: DNA
<213> ORGANISM: Trichoderma reesei

<400> SEQUENCE: 2

```
gctaagactg catgtgcatc acgaaaagtg ggcgcttgat agtcctcctc cagccggcat       60
tggcgaagca ggatagacga tggacaagat gcagcatcag ctcggacgga gccctccctc     120
cctgatgata agccaaaaca ctcttccggt ggcgccatgc aagtacggcg catgttgctc     180
gcagagccaa gtgcagtacc agcagagctg gatcattacc ctacgacttg gaagctgctc     240
gattggcacg gcttgacatg gtcccaaccc ctcaggctgg atgtatttgt gcctcgcacg     300
ctcatcagcg ccctgtccca atggcaatga gtctagattt ggcagcagcg atgtattatc     360
gaacggccag gctcactagg ccaggaacca gtcccgccac agactaccga ctgagagcga    420
gaaatagaga gaggggagaa aggccacagt tgttattacc catggaaatg gctcgtagct    480
gaccacaaca atgatgagga gactgatgat tacgatgtac agtacatacg tattaccact    540
```

```
gccacgagta catacgcacg gggtattaca gctgctgtac caccaggtac ggtcgtgctc      600
gacgctcatt accggtttga tactactggc actagctgca gaggagccat gaacatcaat      660
cgcccagcct gactggtcaa tcaacggccg attcaggggg gacgcaaggg aagcagggaa      720
gcaaggaggc tggggagctc ttggtcgccc tttggggtcc catccgctta ccgctgggtt      780
gcagcatcat gtccgaggag tccactggcg actggagacc cgagtacgcc tgagacgcag      840
cctcgagaga ccagtggccg agacgcctgc tgaggccgct gagcttgcag ggagttgga       900 tgaggttggc tgagtgtggg gacgatgcg gagacgagag gccaggatac gacagcacta      960
ggccggttgt gacgagaata aacaacaaca tggcgagtcc cggggcagg tcgacatgga      1020 gggccgatag gcttaccctc cttggcgagg caacacagcg agcacgccta ggaccgccag     1080
cccggccccc gacctcaaaa gcccatcgag cgtcgtctgc ttccgatctg gttttcctct     1140
cctccagtta tcacagtctc cccgccagaa acaaaggaac aaaagaaaga aagactctc     1200 agaggtatcc aatccctctc tcttttctct ctctcttcga cttttgtttc aggaacaaaa     1260
gcttgaggat ccttcttgtc ttcctttcgt gatcttacgg aaggttgtat gagaagattc    1320
tctcgcgcca gcgcaagccg tcaacctgga ctttgaagcc cgagttcccg tgccctttag    1380
tatcttcccg tccacttaca aggacaacga agcagcacgc cctcagaccc aaatcagcgt    1440
tcacgaggag gttcaactca ccctccctca acacaagcca gccggacggg agggtcaaca    1500
ctcttctttc ccgcaacacg ccgactcagc tcctcctcgc ggcgaacacc gctttgaaga    1560
agaggtccgt atcacgcgtg aggaagaacg tcaccgccgt cccggttccc gccagtctga    1620
acgcttcgtg aaggaagagt tcaagtaagt tgatatttca tttttccctg ctattcatat    1680
tgtctcctgg ctgtggctcc cgcctctcgt ctcctcgcca gaccgctctc accgagtgag    1740
ggcagctggg ggaaaagggg ggagaaaggg atggccaaag gggtgaggag agacgggagg    1800
gagagctggg gaggggtgat gagaacgcac gcagcaatta ccggcgtggc tggcgaaagc    1860
ggtgctgaaa ttacccttcg tattgcccctt cttcccacac agctcttttg ccgcggcttc    1920
tagaacgcgt caattgatag tggggagggc aagcctgggc acggggaggg cggcggagct    1980
cactatgggg agctgacagc cggggtggga gttcagctag gattcccagc catgccaatt    2040
tatcccggct caggggtcc gggggccca ccaatgttgg cccagagacc aaggaagctc       2100
acgcacaggc acaaaaggga atctctccag ctaacctcga gtacttttag atccatccca     2160
cctcctcctc gcgactacac tgagactcaa gtccaagtcg acacttctcg ccgctacacc     2220
aaccccattg acgctgctga gcgtgagtat cgggaacgta tccgtcctca ccacccagag     2280
agctccaccg gcctcgaact agttgttcgc cgtcctcgtc actccgacaa gtctcaccac    2340
caccaccacc acaagtcctc cgacttcacc gttgtcgacg agcacacttc tgttgcccgt    2400
cccaagttcc gtgaggagat caagatcacc gaggaaatcc gcgagtctac tccgcaagtc     2460
cccgaacaat ccgccaagat gggttactac gacgacgagg gtaagctata ctaacgttct    2520
tttgtctctc tccctcccgc tcttctcctc cattccctcc ctgtctggcc agacgcgtgc    2580
aagcatacgc taacgcgtgt cgccggcagg ctcttaccac tccctcaagc acggcgtcgc    2640
caagacgatc gacaagctgc tccctcatca ccaccaccat caccaccaca gtgatcacca    2700
ccaccacagt gaccatcatg accataataa cactacgatc acagagcacg ttgaagttga    2760
tgttgtccgc cacgatgcta atcactcgcg acgcgcagct cccgccactg agtcgcagcc    2820
tcagactgtg tccatcccct gccaccacat ccgcctgggt gacttcctga tgctccaggg    2880
```

```
ccgaccatgc caggtcatcc gcatctcgac ctcgtccgcc actggccagt accgctacct    2940
tggtgttgac ctcttcacca agcagctgca cgaggagtcc tccttcatct ccaaccctgc    3000
ccccagcgtt gttgtccaga ccatgctcgg ccccgtcttc aagcagtacc gcgtcctcga    3060
catggctgac ggctacgtca ccgccatgac cgagaccggc gacgtcaagc agggcctcaa    3120
ggtcattgac cagtccaacc tgtggtctcg tctgcagcag gctttcgagt ccggccgcgg    3180
cagcgtccgt gtcctggtcc tcaacgacgg cggccatgag ctcgctgttg agatgaaggt    3240
cgtccacggc tctcgcctgt aaacaatcct ctcgatgaca tctttcgtgt ctaaggggga    3300
gggtttattg tccatccatc ctatggatat tccaggctcg gatcaagcct gaataatgtg    3360
aaaaatacccc catgggcttg gagtgatacg tggaacggtt tgtcattttt ttggatcggg    3420
ctgggatgta ttttggtcat gaggcagagt gcccagtaga taggatctac ctatgtgcag    3480
cactgtaatt taagatggat tttgcataac ttttttcttt gtgccgccct ttgtgacatg    3540
cagtgatgat gcatcgtgat gcatcgtgtt gtcatggctg taaatcgtcc tccctgcgca    3600
gatcacaagc agtacacgtt gcctcttgac gcgtcgtcgt gttagactac ctgcctacct    3660
acccaatgtc tgcgtgttga catcaaggta cccgtcgcca gcgcaccggt catgggatac    3720
atggggaaac cccacaagat tgcagcagcc acgatattat acgatgcccg acatgtgaga    3780
gtcgatggtc ctcttttttc ccttgctcca aaccccactt gtcgcatctg taacgagaga    3840
ctgacgttgt cttgatatga agcaagcatc gattcagaga cgaggaagca accagcactg    3900
tgctaacatg caacaaata cgagaccaag tggtagatat attacagagc acatataggc    3960
atgtaagcaa tgaggaccgg gcagataggg gaattgctgg agataacatg taggtagcgc    4020
gacaaaagaa ccggtgggat ctggatatag ccgacgaatg atgtgatact aaacttgaag    4080
gagggggggg gaggggagag gggggatgag ggcggggag atgaaaggcc ggataagcag    4140
aggaccagca gacggtccat gttttgttgc ggtagcaaac aacacaacca cgatgttgat    4200
gtgctccaac gactggtttt gataaggtga ttgtttgttt gccttgagat acgtcggctc    4260
ttacagctgt tggcgtgtat atcttgacat catacataag gactccccc cttgttgaat    4320
tgctttttcag cgaaaagacg tacgtagtac tagtaggata taacacgtag ctaggg       4376
```

<210> SEQ ID NO 3
<211> LENGTH: 224
<212> TYPE: PRT
<213> ORGANISM: Trichoderma reesei

<400> SEQUENCE: 3

Met Gly Tyr Tyr Asp Asp Glu Gly Ser Tyr His Ser Leu Lys His Gly
1               5                   10                  15

Val Ala Lys Thr Ile Asp Lys Leu Leu Pro His His His His His His
            20                  25                  30

His His Ser Asp His His His Ser Asp His Asp His Asn Asn
        35                  40                  45

Thr Thr Ile Thr Glu His Val Glu Val Asp Val Val Arg His Asp Ala
    50                  55                  60

Asn His Ser Arg Arg Ala Ala Pro Ala Thr Glu Ser Gln Pro Gln Thr
65                  70                  75                  80

Val Ser Ile Pro Cys His His Ile Arg Leu Gly Asp Phe Leu Met Leu
                85                  90                  95

Gln Gly Arg Pro Cys Gln Val Ile Arg Ile Ser Thr Ser Ser Ala Thr
            100                 105                 110

-continued

```
Gly Gln Tyr Arg Tyr Leu Gly Val Asp Leu Phe Thr Lys Gln Leu His
        115                 120                 125

Glu Glu Ser Ser Phe Ile Ser Asn Pro Ala Pro Ser Val Val Val Gln
        130                 135                 140

Thr Met Leu Gly Pro Val Phe Lys Gln Tyr Arg Val Leu Asp Met Ala
145                 150                 155                 160

Asp Gly Tyr Val Thr Ala Met Thr Glu Thr Gly Asp Val Lys Gln Gly
                165                 170                 175

Leu Lys Val Ile Asp Gln Ser Asn Leu Trp Ser Arg Leu Gln Gln Ala
                180                 185                 190

Phe Glu Ser Gly Arg Gly Ser Val Arg Val Leu Val Leu Asn Asp Gly
        195                 200                 205

Gly His Glu Leu Ala Val Glu Met Lys Val Val His Gly Ser Arg Leu
        210                 215                 220
```